United States Patent
Zhang et al.

(10) Patent No.: US 11,547,565 B2
(45) Date of Patent: Jan. 10, 2023

(54) ARTIFICIAL CHORDAE TENDINEAE AND ARTIFICIAL CHORDAE TENDINEAE IMPLANTATION SYSTEM

(71) Applicant: Hangzhou Valgen Medtech Co., Ltd., Hangzhou (CN)

(72) Inventors: Tingchao Zhang, Hangzhou (CN); Weiwei Zhang, Hangzhou (CN); Chunyuan Zhou, Hangzhou (CN)

(73) Assignee: HANGZHOU VALGEN MEDTECH CO., LTD., Hangzhou (CN)

( * ) Notice: Subject to any disclaimer, the term of this patent is extended or adjusted under 35 U.S.C. 154(b) by 508 days.

(21) Appl. No.: 16/749,188

(22) Filed: Jan. 22, 2020

(65) Prior Publication Data

US 2020/0155315 A1    May 21, 2020

Related U.S. Application Data

(63) Continuation of application No. PCT/CN2018/096901, filed on Jul. 24, 2018.

(30) Foreign Application Priority Data

Jul. 31, 2017    (CN) .......................... 201710640936.4

(51) Int. Cl.
  *A61F 2/24*    (2006.01)
  *A61B 17/34*    (2006.01)

(52) U.S. Cl.
  CPC .......... *A61F 2/2466* (2013.01); *A61F 2/2457* (2013.01); *A61B 17/3468* (2013.01); *A61F 2220/0016* (2013.01)

(58) Field of Classification Search
  CPC ............ A61B 17/0401; A61B 17/0469; A61B 2017/0472; A61B 2017/00243;
  (Continued)

(56) References Cited

U.S. PATENT DOCUMENTS

| 7,335,213 B1 | 2/2008 | Hyde et al. |
| 2007/0118151 A1 | 5/2007 | Davidson |

(Continued)

FOREIGN PATENT DOCUMENTS

| CN | 103251464 A | 8/2013 |
| CN | 103826570 A | 5/2014 |

(Continued)

OTHER PUBLICATIONS

International Search Report with translation for Application No. PCT/CN2018/096901; dated Oct. 11, 2018.
The International Search Report issued corresponding PCT application No. PCT/CN2019/087886 dated Jul. 29, 2019.
The Extended European Search Report issued corresponding EP Application No. EP 18840531.0 dated Apr. 1, 2021.

*Primary Examiner* — George J Ulsh
(74) *Attorney, Agent, or Firm* — Hauptman Ham, LLP

(57) ABSTRACT

An artificial chordae tendineae includes a chordae tendineae main body with at least one end connected to a fixing member. A side of the fixing member facing away from the chordae tendineae main body is provided with a puncturing connection member. An artificial chordae tendineae implantion system includes a clamping device, a puncturing device including a puncture needle, the artificial chordae tendineae, and a pushing device including a pushing shaft. The puncturing device and the clamping device are received in the pushing shaft. A proximal clamp of the clamping device is provided at a distal end of the pushing shaft. A distal clamp of the clamping device is provided at a distal end of the clamping push rod. A distal end of the puncture needle is provided with a tapped straight tip. The artificial chordae tendineae is received in the clamping device. The fixing member corresponds to the puncture needle.

13 Claims, 11 Drawing Sheets

(58) Field of Classification Search
CPC ............. A61B 2017/06042; A61B 2017/0495; A61B 2017/0409; A61B 2017/0406; A61B 17/3468; A61F 2220/0016; A61F 2/2457; A61F 2/2466
See application file for complete search history.

(56) References Cited

U.S. PATENT DOCUMENTS

| | | | |
|---|---|---|---|
| 2009/0105729 A1* | 4/2009 | Zentgraf | A61B 17/0469 606/139 |
| 2011/0060407 A1* | 3/2011 | Ketai | A61F 2/2463 623/2.37 |
| 2013/0110230 A1 | 5/2013 | Solem | |
| 2015/0134057 A1* | 5/2015 | Rourke | A61B 17/0485 623/2.36 |
| 2018/0289480 A1* | 10/2018 | D'ambra | A61F 2/2445 |

FOREIGN PATENT DOCUMENTS

| | | |
|---|---|---|
| CN | 104248457 A | 12/2014 |
| CN | 104367351 A | 2/2015 |
| CN | 104665888 A | 6/2015 |
| CN | 104939949 A | 9/2015 |
| CN | 105246431 A | 1/2016 |
| CN | 107468378 A | 12/2017 |
| CN | 107569301 A | 1/2018 |
| CN | 108186163 A | 6/2018 |
| CN | 109199468 A | 1/2019 |
| WO | 2008112237 A2 | 9/2008 |
| WO | 2011034973 A2 | 3/2011 |
| WO | 2017066888 A1 | 4/2017 |

* cited by examiner

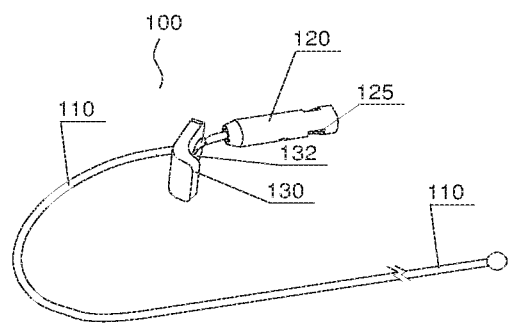
FIG. 5
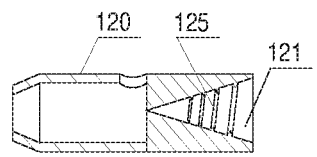 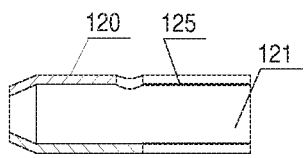
FIG. 6     FIG. 7
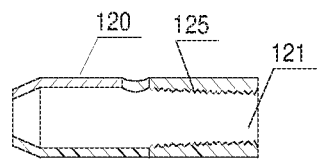 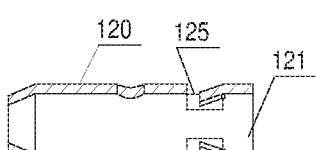
FIG. 8     FIG. 9

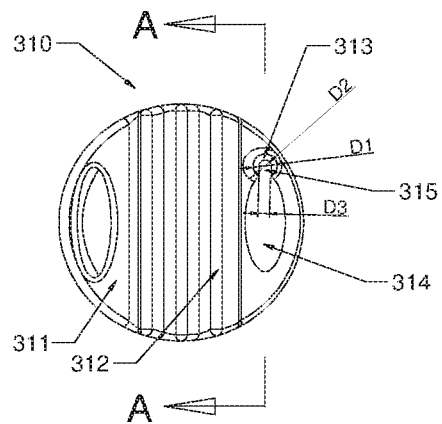
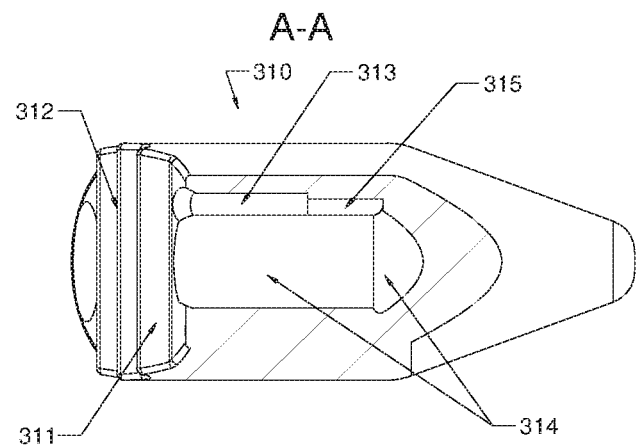
FIG. 22    FIG. 23
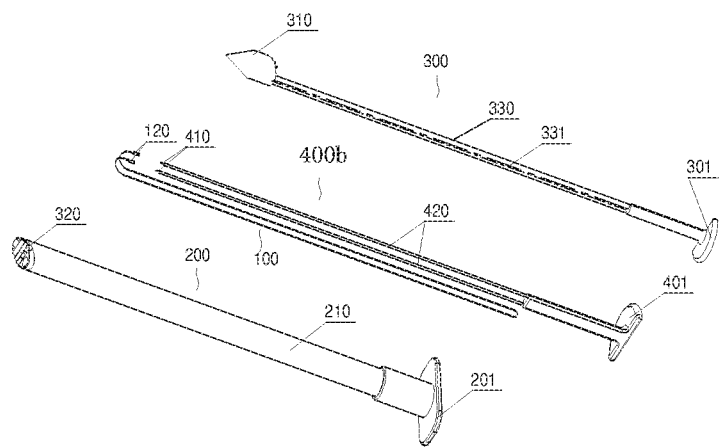
FIG. 24

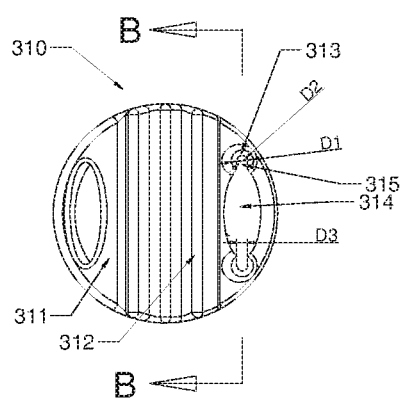
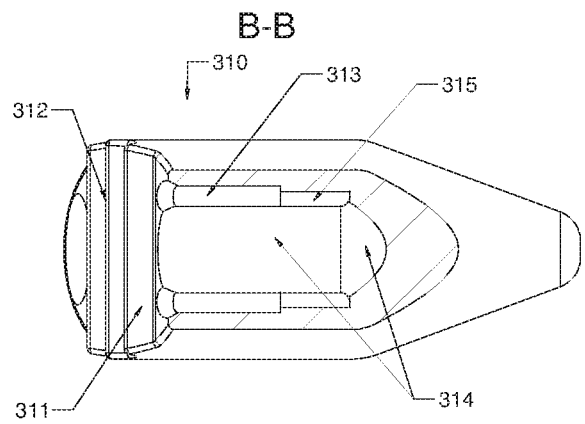
FIG. 25   FIG. 26
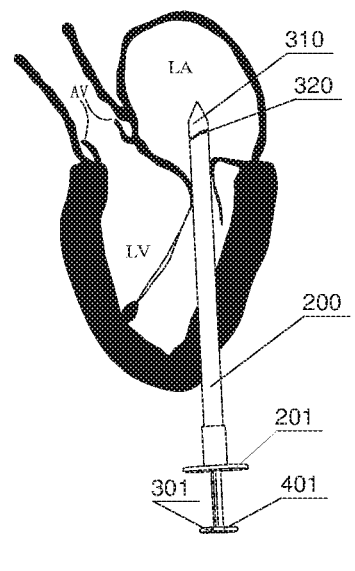
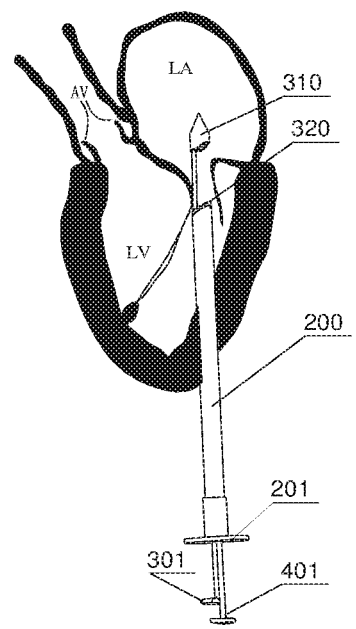
FIG. 27   FIG. 28

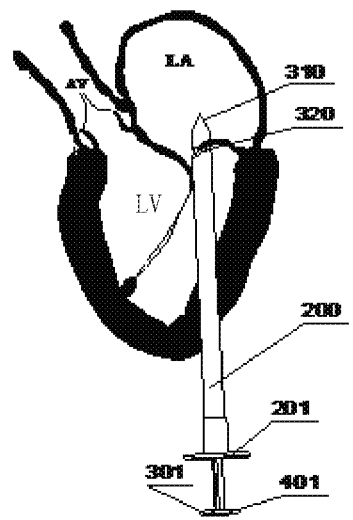 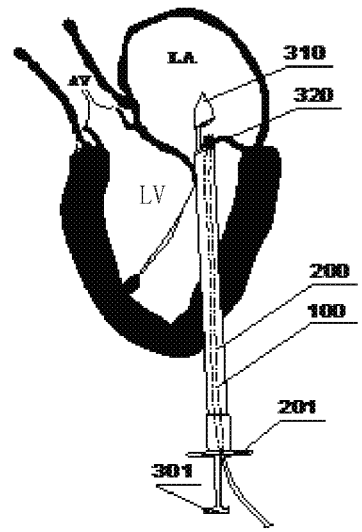
FIG. 29    FIG. 30
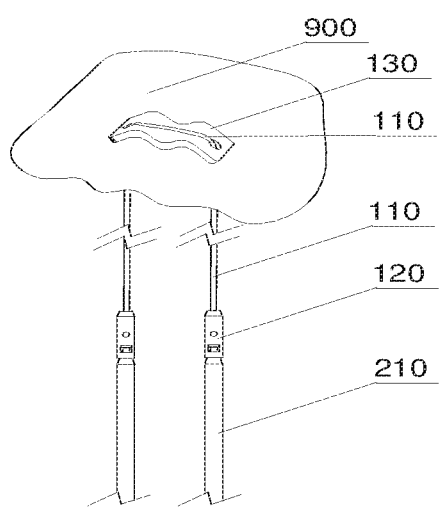
FIG. 31

ARTIFICIAL CHORDAE TENDINEAE AND ARTIFICIAL CHORDAE TENDINEAE IMPLANTATION SYSTEM

CROSS-REFERENCE TO RELATED APPLICATIONS

This application is a continuation of International Application No. PCT/CN2018/096901, filed on Jul. 24, 2018, which claims priority to Chinese Patent Application No. 201710640936.4, filed on Jul. 31, 2017, the content of which is hereby incorporated by reference in its entirety.

FIELD OF THE INVENTION

The present disclosure relates to the field of medical devices, relates to devices for repairing heart valve defeats, and in particular to an artificial chordae tendineae and an artificial chordae tendineae implantation system.

BACKGROUND OF THE INVENTION

The mitral valve is a one-way "valve" between the left atrium (LA) and the left ventricle (LV), which ensures blood flow from the left atrium to the left ventricle. As illustrated in FIG. 1, a normal healthy mitral valve has multiple chordae tendineae (CT). The mitral valve includes an anterior leaflet and a posterior leaflet. When the left ventricle is in a diastolic state, the anterior leaflet and the posterior leaflet are in an open state, and blood flows from the left atrium to the left ventricle. When the left ventricle is in a contracted state, the chordae tendineae are stretched, such that the leaflets will not be rushed into the left atrium by the blood flow. At this time, the anterior leaflet and the posterior leaflet both are well closed, thereby ensuring that blood flows from the left ventricle to the aorta via the aortic valve (AV). If there is a lesion in the chordae tendineae or papillary muscles, such as a rupture of the chordae tendineae of the posterior leaflet as illustrated in FIG. 2, when the left ventricle is in the contracted state, the mitral valve cannot return to a closed state as normal, and the impulse of the blood flow will further cause the leaflet to be rushed into the left atrium, causing blood reflux.

At present, lesions in the chordae tendineae are generally treated by surgically implanting artificial chordae tendineae. However, this requires adopting invasive open thoracotomy approaches, under general anesthesia, and moderate hypothermia cardiopulmonary bypass as an auxiliary support. Such surgical operations have the disadvantages of complicated surgical procedures, high surgical cost, high surgical costs, high degrees of patient trauma, high risks of complications, long hospitalization, and painful recovery processes.

Another treatment is to implant an artificial chordae tendineae in a minimally invasive manner. In prior art, medical devices for implanting the artificial chordae tendineae include a handle assembly, a capture assembly, and a needle. After leaflets are captured by the capture assembly, a needle with a hook-shaped end is used to pass through the leaflet to pick a suture as the artificial chordate as. The needle is then retracted to drive the artificial chordae tendineae to pass through the leaflet, and one end of the artificial chordae tendineae is fixed to a ventricular wall. However, the above medical device has the disadvantages of low probability of the needle picking the artificial chordae tendineae, a low success rate of surgery, and a long surgery time.

SUMMARY OF THE INVENTION

In response to the disadvantages of the prior art, a technical problem to be solved by the present disclosure is to provide an artificial chordae tendineae capable of forming a stable connection with a puncture needle.

A further technical problem to be solved by the present disclosure is to provide an artificial chordae tendineae implantation system capable of reliably connecting an artificial chordae tendineae.

The technical solutions adopted by the present disclosure to solve the above technical problems are the following.

An artificial chordae tendineae includes a flexible chordae tendineae main body and a fixing member. The fixing member is connected to at least one end of the chordae tendineae main body. The fixing member is configured to be connected with a puncture needle. The fixing member includes a puncture connection member disposed at a side of the fixing member facing away from the chordae tendineae main body.

In an illustrative embodiment, the fixing member is provided with an accommodation cavity for accommodating the puncture needle. The puncture connection member is selected from a group consisting of threads, an adhesive layer, a rough surface, and at least one groove or hole disposed on a sidewall of the accommodation cavity. The at least one groove or hole is configured to engage with the puncture needle in an interference fit connection, a snap connection, and a key connection.

In an illustrative embodiment, the chordae tendineae main body is sleeved with an anti-slip member. The anti-slip member slides along an axis of the chordae tendineae main body.

In an illustrative embodiment, the anti-slip member is provided with a through hole, and the chordae tendineae main body extends through the through hole; or the anti-slip member defines a pair of through holes, and two ends of the chordae tendineae main body respectively extend through the through holes; or the anti-slip member defines at least two through holes, and at least two chordae tendineae bodies respectively extend through the at least two through holes.

In an illustrative embodiment, the anti-slip member is blocked by the fixing member.

In an illustrative embodiment, the anti-slip member includes a fitting surface configured to be fitted on a leaflet.

An artificial chordae tendineaeate implantation system includes an artificial chordae tendineae, a pushing device, a clamping device, and a puncturing device. The pushing device includes a pushing shaft. The pushing shaft defines a number of lumens along an axis thereof. The clamping device and the puncturing device are movably received in different lumens of the pushing shaft. The clamping device includes a clamping push rod, a distal clamp, and a proximal clamp. The distal clamp and the proximal clamp cooperatively clamp a leaflet. The proximal clamp is disposed at a proximal end of the pushing shaft. The distal clamp is disposed at a distal end of the clamping push rod. The puncturing device includes a puncture needle. A distal end of the puncture needle is provided with a straight tapered tip. The artificial chordae tendineae is received in the clamping device. The artificial chordae tendineae includes a flexible chordae tendineae main body. At least one end of the chordae tendineae main body is connected with a fixing member which is configured to connect with the puncture needle.

In an illustrative embodiment, the fixing member includes a puncture connection member disposed at a side thereof facing away from the chordae tendineae main body. The puncture needle further includes chordae tendineae connection member configured to be connected with the puncture connection member.

In an illustrative embodiment, the chordae tendineae connection member is disposed at a distal end of the puncture. The chordae tendineae connection member is at least one protruding tooth or a circle of protruding flanges connected with the puncture connection member in an interference fit connection, a snap connection, or a key connection; or the chordae tendineae connection member is threads, an adhesive layer, or a rough surface is disposed on an external surface of the puncture needle.

In an illustrative embodiment, the distal clamp includes a clamping surface dispose at a proximal end of the distal clamp. The puncturing device includes a puncturing push rod connected to the puncture needle. The puncturing push rod is received in the lumens of the pushing shaft. The clamping push rod is provided with an artificial chordae tendineae channel along an axial direction. The distal clamp is provided with an artificial chordate tendineae accommodation chamber which is connected through with the clamping surface of the distal clamp. The artificial chordae tendineae accommodation chamberis connected with the artificial chordae tendineae channel. The artificial chordae tendineae is received in the artificial chordae tendineae channel and the artificial chordae tendineae accommodation chamber.

In an illustrative embodiment, the chordae tendineae main body is sleeved with an anti-slip member sliding along an axial of the chordae tendineae main body. The clamping surface of the distal clamp defines an accommodation slot for accommodating the anti-slip member. The accommodation slot is radially in communication with the artificial chordae tendineae accommodation chamber.

In an illustrative embodiment, the fixing member is received in the distal clamp and the fixing member corresponds to the puncture needle.

In an illustrative embodiment, the clamping surface of the distal clamp defines a fixing cavity for receiving the fixing member. The fixing cavity is axially in communication with the artificial chordae tendineae accommodation chamber. The fixing cavity is radially in communication with the accommodation slot.

In an illustrative embodiment, a shape of the fixing cavity corresponds to a shape of the fixing member. A diameter of an inscribed circle of the fixing cavity is larger than a diameter of a circumscribed circle of the artificial chordae tendineae accommodation chamber.

In an illustrative embodiment, the proximal clamp includes a clamping surface disposed at a distal end of the proximal clamp. The clamping surface of the proximal clamp and the clamping surface of the distal clamp are capable of being fitted together. At least one of the clamping surfaces includes a reinforcing member for increasing clamping forces.

In an illustrative embodiment, the reinforcing member is selected from a group consisting of a protrusion, a ridge, a groove, and a recess provided on the clamping surfaces.

In an illustrative embodiment, the distal clamp includes a clamping surface disposed at a proximal end of the distal clamp. The puncturing device includes a pair of puncture needles and a pair of puncturing push rods connected to the puncture needles respectively. The puncturing push rods are received in the lumens of the pushing shaft. The artificial chordae tendineae is provided with a pair of fixing members respectively disposed at the two ends of the artificial chordae tendineae main body. The two fixing members are received in the distal clamp. The two puncture needles respectively correspond to the two fixing members.

In an illustrative embodiment, the clamping push rod is provided with an artificial chordae tendineae channel along an axial direction. The distal clamp is provided with a pair of artificial chordae tendineae accommodation chambers which are connected through with the clamping surface of the distal clamp. The pair of artificial chordae tendineae accommodation chambers is connected with the artificial chordae tendineae channel. The pair of artificial chordae tendineae accommodation chambers are radially connected with each other. The two ends of the chordae tendineae main body extend through the artificial chordae tendinea channel and the two artificial chordae tendinea accommodation chambers to be connected with the two fixing members, respectively.

In an illustrative embodiment, the clamping surface of the distal clamp defines a pair of fixing cavities for respectively receiving the fixing members. Each of the fixing cavities is axially in communication with the pair of artificial chordae tendineae accommodation chambers. The pair of the fixing cavities are radially in communication with each other.

In an illustrative embodiment, the chordae tendineae main body of the artificial chordae tendineae is sleeved with an anti-slip member. The anti-slip member defines a pair of through holes for two ends of the chordae tendineae main body extending therethrough respectively.

In an illustrative embodiment, the clamping surface of the distal clamp defines a pair of fixing cavities for receiving the pair of fixing members and an accommodation slot for accommodating the anti-slip member. Each of the fixing cavities is radially in communication with the accommodation slot. The accommodation slot is radially in communication with the artificial chordae tendineae accommodation chamber.

In an illustrative embodiment, the proximal end of the pushing shaft is provided with a first handle, and a proximal end of the clamping push rod is provided with a second handle. A proximal end of the puncturing device is provided with a third handle. The second handle drives the clamping device to move along an axis of the pushing shaft. The third handle drives the puncture needle to move along the axis of the pushing shaft.

Compared with the prior art, the present disclosure at least has the following advantages.

At least one end of the chordae tendineae main body of the artificial chordae tendineae of the present disclosure is provided with the fixing member configured to be connected with the puncture needle. In this way, although the puncture needle and the artificial chordae tendineae are not directly connected, the artificial chordae tendineae is connected with the puncture needle via the fixing member. Therefore, reliability of the connection between the artificial chordae tendineae and the puncture needle is improved. During retracing of the puncture needle, the artificial chordae tendineae can be prevented from falling off from the puncture needle.

In the artificial chordae tendineae implantation system of the present disclosure, the puncture needle is provided with the straight tapered tip. Compared with a hook-shaped puncture needle in prior art, the puncture needle of the present disclosure has a smaller puncturing point formed on the leaflet. The diameter of the puncturing point is controlled to range from 0.3 mm to 1.5 mm. Thus, damage to the leaflet is reduced and postoperative healing process is accelerated.

The fixing member of the artificial chordae tendineae and the puncture needle are positioned via the clamping device. In this way, the probability of successful connection between the puncture needle and the fixing member is effectively increased, and accordingly the surgery time is reduced. In addition, the stable and reliable indirect connection between the puncture needle and the artificial chordae tendineae is formed. In this way, the artificial chordae tendineae is not easily released from the puncture needle, and the artificial chordae tendineae can be easily pulled to fixed positions.

BRIEF DESCRIPTION OF THE DRAWINGS

To illustrate the technical solutions of embodiments of the present disclosure more clearly, the accompanying drawings in the embodiments are introduced in the following. Obviously, the described accompanying drawings merely illustrate embodiments of the present disclosure. Those skilled in the art may obtain other accompanying drawings according to the described accompanying drawings without creative efforts.

FIG. 5 is a schematic diagram of the structure of an artificial chordae tendineae according to a third implementation of the present disclosure.

FIGS. 6 to 9 are schematic diagrams of the structure of a fixing member of an artificial chordae tendineae according to different implementations of the present disclosure.

FIG. 22 is a schematic diagram of the structure of a clamping surface of a distal clamp of an artificial chordae tendineae implantation system according to a first embodiment of the present disclosure.

FIG. 23 is a cross-sectional view of the distal clamp taken along a line A-A of FIG. 22.

FIG. 24 is an exploded view of an artificial chordae tendineae implantation system according to a second embodiment of the present disclosure.

FIG. 25 is a schematic diagram of the structure of a clamping surface of a distal clamp of an artificial chordae tendineae implantation system according to a second embodiment of the present disclosure.

FIG. 26 is a cross-sectional view of the distal clamp taken along a line B-B of FIG. 25.

FIGS. 27 to 32 are schematic diagrams of the process of using the artificial chordae tendineae implantation system according to the second embodiment to implant an artificial chordae tendineae into a heart.

DETAILED DESCRIPTION OF THE INVENTION

The present disclosure will be described in details in combination with the accompanying drawings and embodiments such that the purpose, technical solution and advantages of the present disclosure will be more apparent.

For the sake of facilitation of illustrating, in the field of invasive medical device technology, a position near the operator is defined as a proximal end, and a position away from the operator is defined as a distal end.

Figure 1:
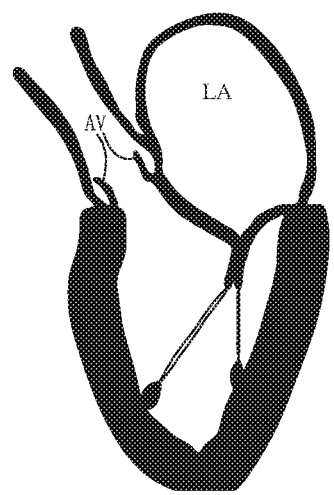
FIG. 1 is a schematic diagram illustrating normal chordae tendineae in a heart.
Figure 2:
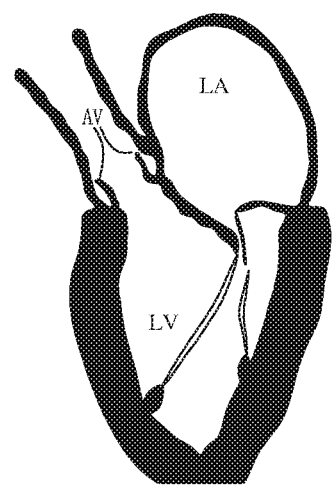
FIG. 2 is a schematic diagram illustrating ruptured chordae tendineae in a heart.
Figure 3:
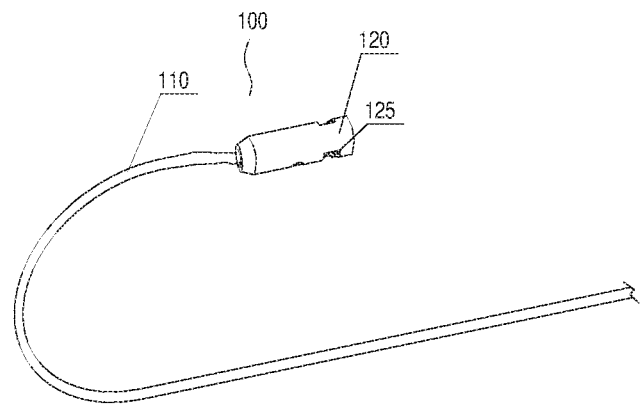
FIG. 3 is a schematic diagram of the structure of an artificial chordae tendineae according to a first implementation of the present disclosure.

As illustrated in FIG. 3, an artificial chordae tendineae 100 of the present disclosure includes a flexible chordae tendineae main body 110. The chordae tendineae main body 110 has a certain axial length. The chordae tendineae main body 110 is configured to be implanted into a heart to replace a diseased natural chordate tendineae. The chordae tendineae main body 110 has two opposite ends, that is, a first end and a second end opposite the first end. The first end of the chordae tendineae main body 110 is connected with a fixing member 120. A side of the fixing member 120 facing away from the chordae tendineae main body 110 is provided with a puncture connection member which is configured for a detachable or non-detachable connection with a puncture needle.

One end of the chordae tendineae main body 110 may be fixed on a leaflet, and the other end of the chordae tendineae main body 110 may be fixed on a ventricular wall or papillary muscle. The chordae tendineae main body 110 is configured to replace the diseased nature chordate tendineae, thereby maintaining the tension between the leaflet and the ventricular wall or the papillary muscle. A flexible chordae tendineae main body 110 means that it can be bent freely in the axial direction thereof without stretching. Generally, the chordae tendineae main body 110 is in the form of a flexible wire. The material of the chordae tendineae main body 110 may be a polymer materials compatible with a human body or relatively soft metal materials, particularly a polymer material.

The first end and the second end of the chordae tendineae main body 110 have no difference in direction, importance, and the like.

As illustrated in FIG. 3, the fixing member 120 may be disposed at either end of the chordae tendineae main body 110.

Figure 4:
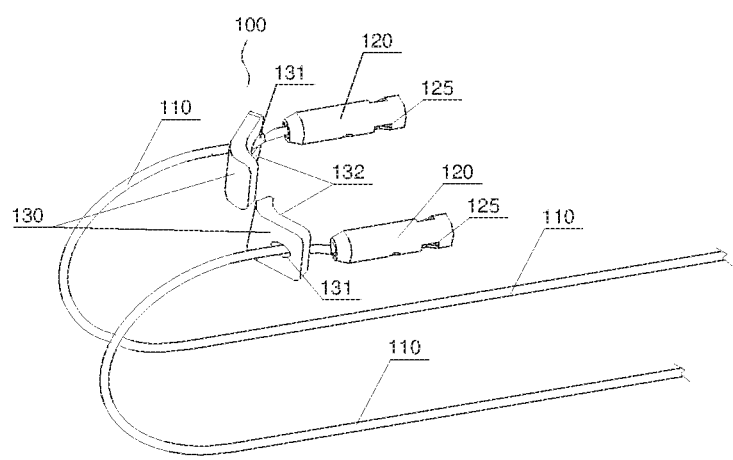
FIG. 4 is a schematic diagram of the structure of an artificial chordae tendineae according to a second implementation of the present disclosure.

As illustrated in FIG. 4, each end of the chordae tendineae main body 110 may be provided with a fixing member 120.

The chordae tendineae main body 110 may be connected with the fixing member 120 by tying, winding, welding, bonding, snap fitting, or the like. For example, one end of the chordae tendineae main body 110 may pass through the fixing member 120 and then tied to form a larger diameter coil, or the end may be welded to form a large diameter ball, or the end may be provided with a positioning rod. In a natural state, the positioning rod has a different axis from the chordae tendineae main body 110 and the fixing member 120. After the positioning rod and the corresponding end of the chordae tendineae main body 110 pass through the fixing member 120, the positioning rod returns to the natural state and snappingly blocks a back side of the fixing member 120, thereby fixing the corresponding end of the chordae tendineae main body 110 to the fixing member 120.

As illustrated in FIG. 5, when one end of the chordae tendineae main body 110 is provided with the fixing member 120, and other end of the chordae tendineae main body 110 is not provided with the fixing member 120, the other end of the chordae tendineae main body 110 may, by way of tying, winding, or providing a spherical end, a disc-shaped end, or the like, have a cross-sectional dimension greater than a cross-sectional dimension of the chordae tendineae main body 110, thereby blocking the other end of the chordae tendineae main body 110 on an upper surface of the leaflet.

As illustrated in FIGS. 6 to 9, a detachable or a non-detachable connection may be formed between the fixing member 120 and the puncture needle. The fixing member 120 has a shape corresponding to the corresponding connection. Since a distal end of the puncture needle is generally provided with a sharp tapped straight tip, a contact area between the puncture needle and an external surface of the fixing member 120 should be as large as possible, thereby forming a stable connection between the fixing member 120 and the puncture needle. The side of the fixing member 120 facing away from the chordae tendineae main body 110 is provided with an accommodation cavity 121 for accommodating the puncture needle. A shape of the accommodation cavity 121 corresponds to a shape of the distal end of the puncture needle. The accommodation cavity 121 is generally tapered or cylindrical, and the fixing member 120 is generally cylindrical. The fixing member 120 may has a cross section in a round, elliptical, polygonal shape. In an illustrated embodiment, the fixing member 120 has a cross section in a round or elliptical shape.

The artificial chordae tendineae accommodation chamber 121 is provided with a puncture connection member 125 configured to be connected with the puncture needle. The puncture connection member 125 is embodied in a number of implementations as the following.

As illustrated in FIG. 6, the puncture connection member 125 according to a first implementation of the present disclosure is internal threads defined in a sidewall of the accommodation cavity 121 and configured to engage with the puncture needle. Accordingly, an external surface of the puncture needle defines external threads to engage with the internal threads of the fixing member 120.

As illustrated in FIG. 7, the puncture connection member 125 according to a second implementation of the present disclosure is an adhesive layer provided on the sidewall of the accommodation cavity 121 and configured to be adhered to the puncture needle. For example, the sidewall of the accommodation cavity 121 is provided with biocompatible adhesives to form the adhesive layer. The external surface of the puncture needle is adhered to the fixing member 120 via the adhesive layer, and thus a non-detachable connection between the puncture needle and the fixing member 120 is formed.

As illustrated in FIG. 8, the puncture connection member 125 according to a third embodiment of the present disclosure is a rough surface provided on the sidewall of the accommodation cavity 121 and configured to be frictionally connected with the puncture needle. In an illustrated embodiment, the external surface of the puncture needle is provided with a rough surface to engage the rough surface of the sidewall of the accommodation cavity 121. Thus, a detachable connection between the puncture needle and the fixing member 120 is formed by friction. The rough surfaces may be obtained by providing a number of tiny protrusions or ridges on the sidewall of the accommodation cavity 121 and/or the external surface of the puncture needle. Or, the rough surfaces may be obtained by directly roughening the sidewall of the accommodation cavity 121 and/or the external surface of the puncture needle. Or, the sidewall of the accommodation cavity 121 and/or the external surface of the puncture needle may be made of materials with a certain coefficient of friction to obtain the rough surfaces.

As illustrated in FIG. 9, the puncture connection member 125 according to a fourth implementation of the present disclosure is at least one groove or hole defined in the sidewall of the accommodation cavity 121 and configured to engage with the puncture needle in an interference fit connection, a snap connection, or a key connection.

The interference fit connection refers to a shape of the groove or the hole provided in the sidewall of the accommodation cavity 121 corresponding to a shape of the puncture needle and the groove or the hole provided in the sidewall of the accommodation cavity 121 engaging with the puncture needle under an interference fit. Thus, a detachable connection between the fixing member 120 and the puncture needle is formed.

The snap connection refers to the groove or the hole provided in the sidewall of the accommodation cavity 121 engaging with the protrusions or the ridges provided on the puncture needle to form a non-detachable or detachable connection. In this embodiment, as illustrated in FIG. 9, at least one groove 125 is radially defined in the sidewall of the accommodation cavity 121 of the fixing member 120 to engage with the protrusions provided on the puncture needle. It can be understood that, the hole or the groove may be a blind hole or a through hole as long as a shape of the hole or the groove may substantially corresponds to a shape of the protrusion or the ridges provided on the puncture needle to form the snap connection. In this embodiment, three recesses 125 are defined in the fixing member 120, such that stability of the connection between the fixing member 120 and the puncture needle is improved, and shaking amplitude of the puncture needle connected with the fixing member 120 is reduced.

The key connection may be a flat key connection, a spline key connection, and the like. The key connection may form a tight key connection, and accordingly force may also be transmitted along an axial direction of the puncture needle. The key connection structure is well known in art, and details are not described herein.

Figure 10:
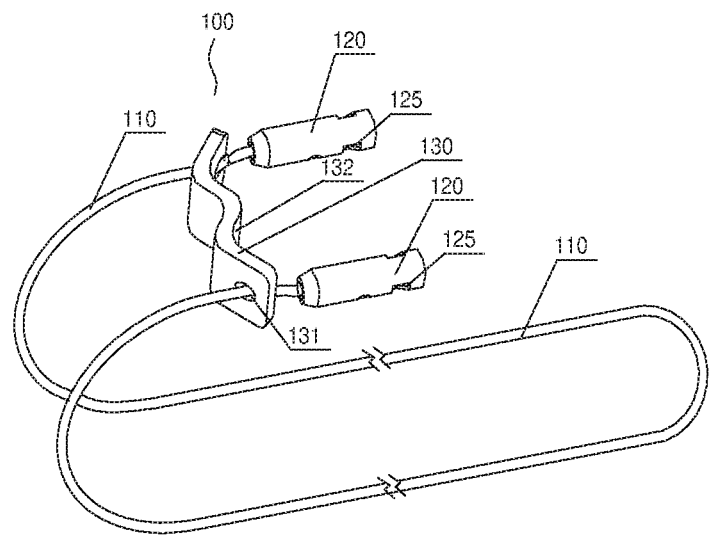
FIG. 10 is a schematic diagram of the structure of an artificial chordae tendineae according to a fourth implementation of the present disclosure.

As illustrated in FIGS. 4, 5, 10, a contact between the artificial chordae tendineae 100 and the leaflet is changed from point contact to face contact to increase contact area, so as to effectively reduce the risk of tearing the artificial chordae tendineae 100. In an illustrated embodiment, the chordae tendineae main body 110 is sleeved with an anti-slip member 130. The anti-slip member 130 may slide along the chordae tendineae main body 110 and be blocked by the fixing member 120. After the anti-slip member 130 is disposed on the artificial chordae tendineae 100, the puncture needle punctures the leaflet and is connected with the artificial chordae tendineae 100. The anti-slip member 130 can be driven to a puncturing point. The anti-slip member 130 together with the artificial chordae tendineae 100 is fixed on the leaflet. The anti-slip member 130 is attached to the artificial chordae tendineae 100 as follows. A through hole 131 is provided in the anti-slip member 130 for the chordae tendineae main body 110 passing through. When the first end of the chordae tendineae main body 110 is provided with the fixing member 120 and the second end of the chordae tendineae main body 110 is not provided with the fixing member 120, the second end is knotted, wound, or provided with a spherical end, a disc-shaped end, or the like, such that the second end has a cross section larger than that of the through hole 131 defined in the anti-slip member 130.

As illustrated in FIG. 4, two chordae tendineae bodies 110 are provided. Each chordae tendineae main body 110 is provided with an anti-slip member 130. Each anti-slip member 130 defines a through hole 131 for one chordae tendineae main body 110 to pass through.

As illustrated in FIG. 10, the anti-slip member 130 defines at least two through holes 131 therein for the first end and the second end of the chordae tendineae main body 110 respectively to pass through.

In other implementations, the anti-slip member 130 defines at least two through holes 131 therein respectively for at least two chordae tendineae bodies 110 of two artificial chordae tendineaes 100 to pass through, that is, at least two artificial chordae tendineaes 100 share one anti-slip member 130.

To prevent the anti-slip member 130 from falling off from the artificial chordae tendineae 100, the through hole 131 has a cross section smaller than that of the fixing member 120. For example, when the through hole 131 of the anti-slip member 130 is a round hole and the fixing member 120 is cylindrical, a diameter of the through hole 131 of the anti-slip member 130 is less than that of the fixing member 120. The end of the chordae tendineae main body 110 without the fixing member 120 should be knotted, or provided with a spherical end, a disc-shaped end, or the like, such that a diameter of this end is larger than that of the through hole 131 of the anti-slip member 130, as illustrated in FIG. 5.

In order to spread force applied to the leaflet by the chordae tendineae main body 110 on a contact area between the anti-slip member 130 and the leaflet, and accordingly the anti-slip member 130 needs to be in contact with the leaflet as much as possible. Thus, the anti-slip member 130 is provided with a fitting surface 132 that fits the leaflet. Except for the fitting surface 132, the specific structure of the anti-slip member 130 may be not limited, may be a sheet shape, a disk shape or a spherical shape, or even an irregular shape having a certain area, and is preferably a sheet shape. The anti-slip member 130 may have a non-porous structure, a mesh structure, a bar-like structure, or the like. The anti-slip member 130 can be made of biocompatible materials, either of elastic materials or non-elastic materials. The anti-slip member 130 may be selected from a group consisting of an elastic pledget, a heart patch, a felt sheet, a mesh structure, a disc-like structure, or a double disc-like structure. The structure of the anti-slip member 130 having the disk-like structure or the double-disc structure is similar to an occluder in prior art, and will not be described herein. To reduce an overall size of the artificial chordate tendineae, the anti-slip member 130 having a disc-like structure or a double disc-like may be made of shape memory materials.

Compared with the related art, the artificial chordae tendineae of the present disclosure has advantages as follows.

At least one end of the chordae tendineae main body is provided with the fixing member configured to be connected with the puncture needle, such that a detachable connection or a non-detachable connection between the chordae tendineae main body and the puncture needle is formed. In this way, although there is no direct contact between the puncture needle and the artificial chordae tendineae, the artificial chordae tendineae, the fixing member, and the puncture needle are sequentially connected via the connection between the puncture needle and the fixing member. Thus, reliability of the connection between the artificial chordae tendineae and the puncture needle is improved and the artificial chordae tendineaeate may be prevented from falling off from the puncture needle.

Figure 11:
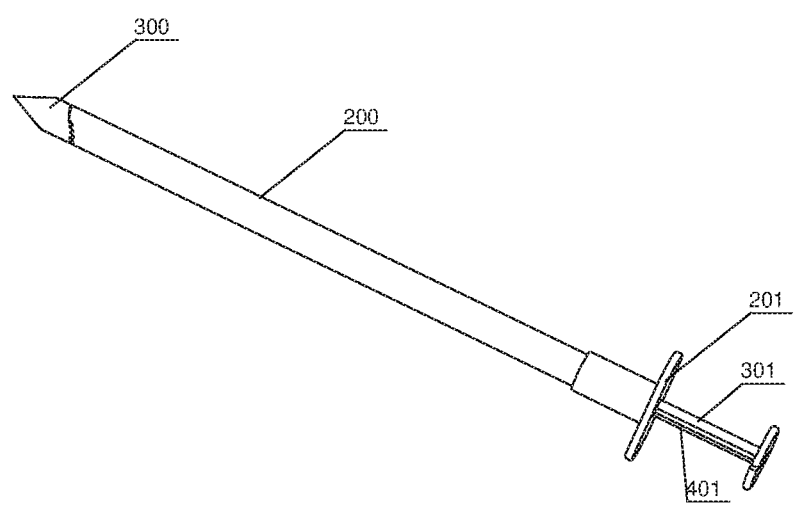
FIG. 11 is a schematic diagram of the structure of an artificial chordae tendineae implantation system according to a first embodiment of the present disclosure.

As illustrated in FIGS. 11 to 23, an artificial chordae tendineae implantation system according to a first embodiment of the present disclosure is configured to implant the artificial chordae tendineae 100 into a heart to replace a diseased natural chordae tendineae. The artificial chordae tendineae implantation system according to the first embodiment of the present disclosure includes the artificial chordae tendineae 100, a clamping device 300, a puncturing device 400a, and a pushing device 200. The pushing device 200 includes a pushing shaft 210. The pushing shaft 210 is provided with a number of lumens 211 in an axial direction of the pushing shaft 210. The puncturing device 400a and the clamping device 300 are movably received in different lumens 211 of the pushing shaft 210, respectively. The clamping device 300 includes a clamping push rod 330, a distal clamp 310, and a proximal clamp 320. The lumens 211 extends through the proximal clamp 320, as illustrated in FIG. 11. The distal clamp 310 and proximal clamp 320 cooperate to clamp the leaflet therebetween. The proximal clamp 320 is disposed at a distal end of the pushing shaft 210. The distal clamp 310 is disposed at a distal end of the clamping push rod 330. The puncturing device 400a includes a puncture needle 410 and a puncturing push rod 420 coupled to a proximal end of the puncture needle 410. A distal end of the puncture needle 410 has a straight tapered tip. The artificial chordae tendineae 100 is received in the clamping device 300. The fixing member 120 of the artificial chordae tendineae 100 corresponds to the puncture needle 410 of the puncturing device 400a.

The artificial chordae tendineae 100 is further provided with the anti-slip member 130. Contact between the artificial chordae tendineae 100 and the leaflet is changed from point contact to face contact. The chordae tendineae main body 110 is provided with at least one anti-slip member 130. The anti-slip member 130 can smoothly slide along the chordae tendineae main body 110 and cannot slip off from the chordae tendineae main body 110 due to being blocked by the fixing member 120. Due to the anti-slip member 130, contact between the artificial chordae tendineae 100 and the leaflet is face contact rather than point contact. In this way, risk of the artificial chordae tendineae 100 tearing the leaflet is effectively reduced.

Figure 12:
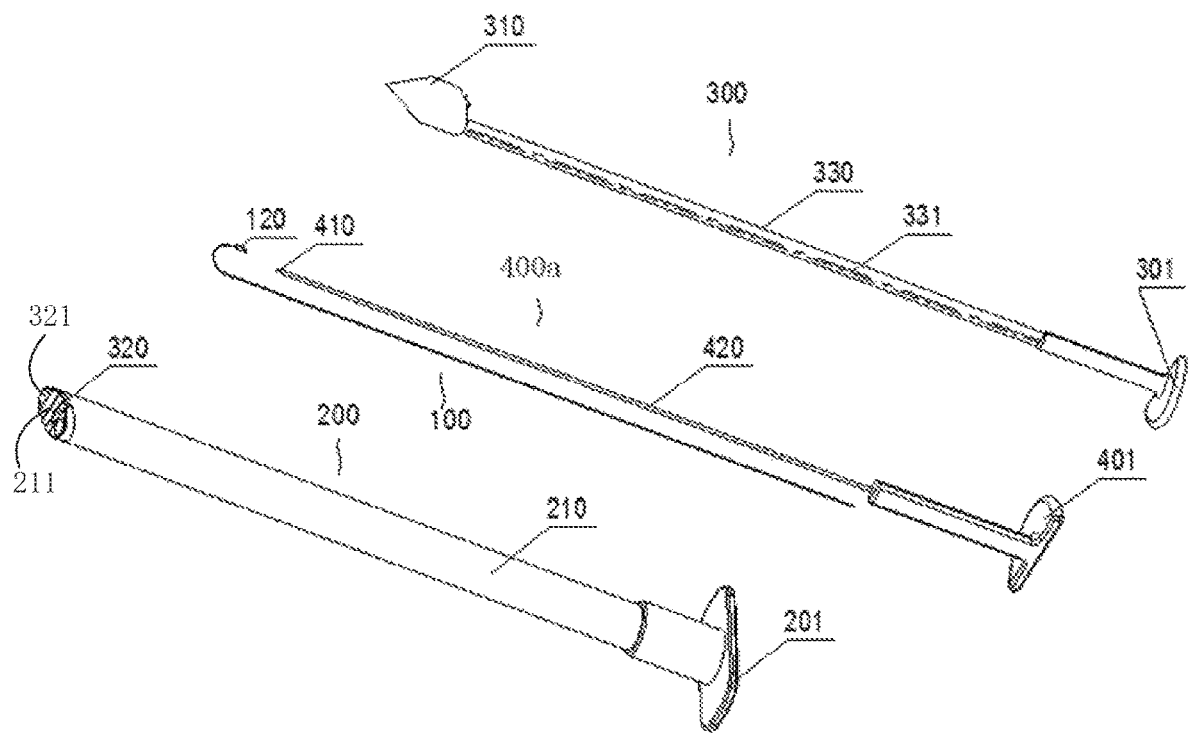
FIG. 12 is an exploded view of an artificial chordae tendineae implantation system according to a first embodiment of the present disclosure.

As illustrated in FIG. 12, the pushing device 200 includes the pushing shaft 210. The pushing shaft 210 is a tube having a certain length. The lumens 211 in the pushing shaft 210 are separated from each other. The pushing shaft 210 can be an integrally formed. The pushing shaft 210 may be formed via a number of internal tubes each with a small size being mounted in an external tube with a larger size. The pushing shaft 210 can be made of biocompatible polymer materials, metal materials, or metal-polymer composite materials. The polymer materials may be polyoxymethylene (POM), polyethylene (PE), nylon (PA), polyvinyl chloride (PVC), acrylonitrile-butadiene-styrene copolymer (ABS), elastomer pebax, or polyurethane (PU), or the like. The metal materials may be stainless steel or nickel-titanium alloy. The proximal end of the pushing shaft 210 is provided with a first handle 201 for manipulating the pushing shaft 210 to move toward the distal end or withdraw toward the proximal end.

The puncture needle 410 is configured to puncture the leaflet. The puncture needle 410 is connected to the fixing member 120 of the artificial chordae tendineae 100 to facilitate driving the chordae tendineae main body 110 toward the proximal end. The distal end of the puncture needle 410 is provided with the straight tapered tip, which facilitates puncture of the leaflet and reduces a size of a puncturing point formed on the leaflet. Compared with the hook-shaped needle in the related art, the puncture needle 410 with the straight tapered tip forms a smaller puncturing point on the leaflet, thereby facilitating postoperative healing of the patient. In this embodiment, the puncturing point formed on the leaflet has a diameter ranging from 0.3 mm to 1.5 mm. Furthermore, by setting a suitable shape and a diameter of the puncture needle 410, the diameter of the puncturing point may controlled to be about 0.7 mm.

The puncture needle 410 is further provided with a chordae tendineae connection member 411 corresponding to the puncture connection member 125 of the artificial chordae tendineae 100 to form a stable and reliable connection between the artificial chordae tendineae 100 and the puncture needle 410. The chordae tendineae connection member 411 is configured to increase the reliability of the connection between the puncture needle 410 and the artificial chordae tendineae 100. The chordae tendineae connection member 411 is embodied as the following implementations.

Figure 14:
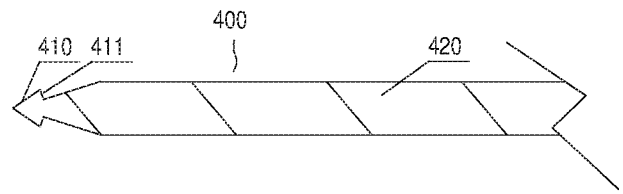
FIG. 14 is a schematic diagram of the structure of a first implementation of a puncture needle of an artificial chordae tendineae implantation system according to a first embodiment of the present disclosure.
Figure 15:
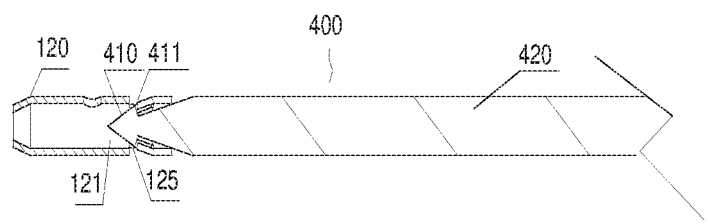
FIG. 15 is a schematic diagram of the structure illustrating the puncture needle of the artificial chordae tendineae implantation system illustrated in FIG. 14 connected with a fixing member of an artificial chordae tendineae.

As illustrated in FIGS. 14 to 15, the chordae tendineae connection member 411 according to a first implementation of the present disclosure is a protruding tooth or a circle of protruding flanges disposed at the distal end of the puncture needle 410 and configured to engage with the fixing member 120 in an interference fit connection, a snap connection, or a key connection.

After puncturing, the accommodation cavity 121 provided at the side of the fixing member 120 faces away from the chordae tendineae main body 110, which allows the puncture needle 410 to be inserted accommodation cavity 121 to tightly engage with the fixing member 120, that is, an interference fit connection is formed between the fixing member 120 of the puncture needle 410. In an illustrative embodiment, the chordae tendineae connection member 411 is a protruding tooth or a circle of protruding flanges disposed next to the tapped straight end of the puncture needle 410.

It can be understood that, in other embodiments, an external surface of the puncture needle 410 next to the tapped straight tip is provided with at least one protruding tooth or a circle of protruding flanges as the puncture connection member 125, corresponding to the hole or groove defined in the sidewall of the accommodation cavity 121 of the fixing member 120. The at least one protruding tooth or circle of protruding flanges is slightly larger than the groove or the hole. As such, an interference fit connection between the puncture needle 410 and the fixing member 120 is formed.

As illustrated in FIG. 15, a snap connection between the puncture needle 410 and the fixing member 120 may be formed. A portion of the puncture needle 410 next to the tapped straight tip or a circle of the puncture needle 410 next to the tapped straight tip is removed, such that the tapped straight tip forms the at least one protruding tooth or the circle of protruding flanges as the chordae tendineae connection member 411. Accordingly, the fixing member 120 of the artificial chordae tendineae 100 is provided with the groove or the hole as the puncture connection member 125. After puncturing, the at least one protruding tooth or the circle of protruding flanges of the puncture needle 410 engage with the groove or the hole of the fixing member 120, and accordingly detachable connection between the puncture needle 410 and the fixing member 120 is formed.

The at least one protruding tooth or the circle of protruding flanges as the chordae tendineae connection member 411 engage with the puncturing connection member 125 of the artificial chordae tendineae 100, and thus a tight key connection between the puncture needle 410 and the fixing member 120 is formed.

Figure 16:
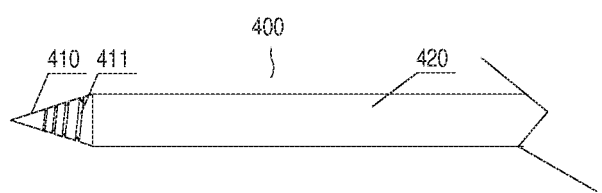
FIG. 16 is a schematic diagram of the structure of a second implementation of a puncture needle of an artificial chordae tendineae implantation system according to a first embodiment of the present disclosure.
Figure 17:
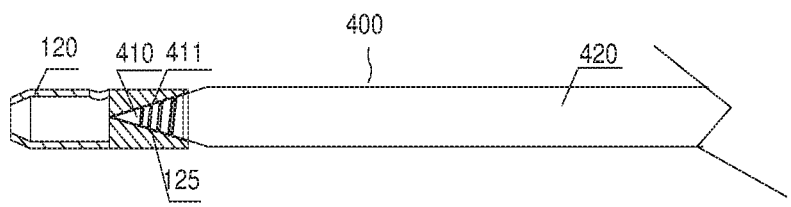
FIG. 17 is a schematic diagram of the structure illustrating the puncture needle illustrated in FIG. 16 connected with a fixing member of an artificial chordae tendineae.

As illustrated in FIGS. 16 to 17, the chordae tendineae connection member 411 according to a second implementation of the present disclosure is external threads provided on the external surface of the puncture needle 410 to threadedly engage with the fixing member 120. For example, at least part of the puncture needle 410 is provided with external threads. In an illustrative embodiment, the puncture needle 410 is provided with the external threads next to the tapped straight end. After puncturing, the puncture needle 410 threadedly engages with the fixing member 120 of the artificial chordae tendineae 100, and thus a detachable connection between the puncture needle 410 and the fixing member 120 is formed, as illustrated in FIG. 17.

Figure 18:
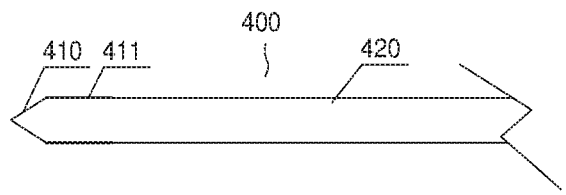
FIG. 18 is a schematic diagram of the structure of a third implementation of a puncture needle of an artificial chordae tendineae implantation system according to a first embodiment of the present disclosure.
Figure 19:
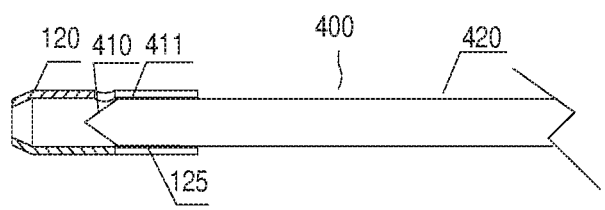
FIG. 19 is a schematic diagram of the structure illustrating the puncture needle illustrated in FIG. 18 connected with a fixing member of an artificial chordae tendineae.

As illustrated in FIGS. 18 to 19, the chordae tendineae connection member 411 according to a third implementation of the present disclosure is an adhesive layer provided on the external surface of the puncture needle 410. For example, biocompatible adhesives are applied to at least part of the external surface of the puncture needle 410 to form the adhesive layer. After puncturing, the fixing member 120 is adhered to the adhesive layer of the puncture needle 410. Thus, a non-detachable connection between the puncture needle 410 and the fixing member 120 is formed, as illustrated in FIG. 19.

Figure 20:
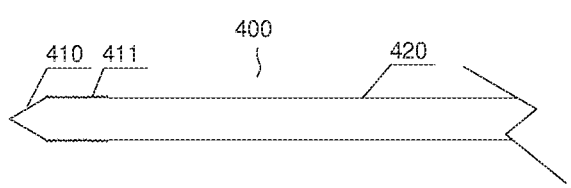
FIG. 20 is a schematic diagram of the structure of a fourth implementation of a puncture needle of an artificial chordae tendineae implantation system according to a first embodiment of the present disclosure.
Figure 21:
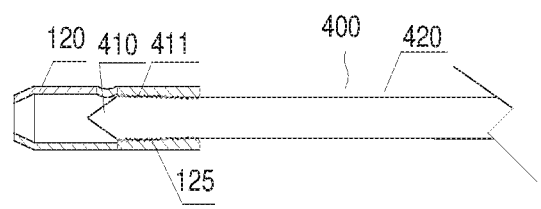
FIG. 21 is a schematic diagram of the structure illustrating the puncture needle illustrated in FIG. 20 connected with a fixing member of an artificial chordae tendineae.

As illustrated in FIGS. 20 to 21, the chordae tendineae connection member 411 according to a fourth implementation of the present disclosure is a rough surface provided on the external surface of the puncture needle 410 and configured to frictionally engage with the fixing member 120. For example, the rough surface is provided on the external surface of at least part of the puncture needle 410. After puncturing, the rough surface of the puncture needle 410 frictionally engages with the rough surface of the fixing member 120 of the artificial chordae tendineae 100 as the puncture connection member 125 to fix the artificial chordae tendineae 100 and the puncture needle 410 together. The rough surface may be formed by a number of tiny protrusions or ridges provided on the external surface of the puncture needle 410 next to the tapped straight end. The external surface of the puncture needle 410 next to the tapped straight end may be directly roughened to obtain the rough surface. The sidewall of the accommodation cavity 121 or the external surface of the puncture needle 410 next to the straight end may be made of materials with a certain coefficient of friction. After puncturing, a detachable connection between the puncture needle 410 and the fixing member 120 is formed, as illustrated in FIG. 21.

As illustrated in FIG. 12, the puncturing push rod 420 is connected to the proximal end of the puncture needle 410. A third handle 401 is provided at the proximal end of the puncturing push rod 420. The puncturing push rod 420 is movably received in the pushing shaft 210. A proximal end of the third handle 401 extends through the proximal end of the pushing shaft 210. The puncturing push rod 420 can be moved along an axial direction of the pushing shaft 210 by operating the third handle 401 to move axially. The puncture needle 410 is driven to puncture toward the distal end or withdraw toward the proximal end. After the leaflet is clamped, the puncture needle 410 is driven by the third handle 401 to puncture the leaflet. After being connected to the fixing member 120 of the artificial chordae tendineae 100, the puncture needle 410 and the artificial chordae tendineae 100 are connected as a whole via the fixing member 120.

Figure 13:
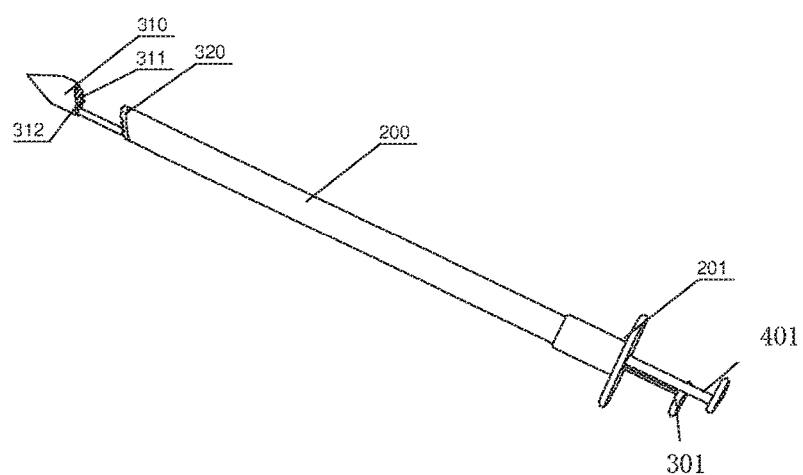
FIG. 13 is a schematic diagram of the structure of an artificial chordae tendineae implantation system according to a first embodiment of the present disclosure, where the artificial chordae tendineae implantation system is in a using state.

As illustrated in FIGS. 11 to 13, the proximal end of the clamping push rod 330 extends through the proximal end of the pushing shaft 210 and is provided with a second handle 301. The clamping push rod 330 is moved toward the distal end via pushing the second handle 301 toward the distal end, such that the distal clamp 310 is moved away from the proximal clamp 320, that is, the clamping device 300 in an open state, as illustrated in FIG. 13. At this time, a distal end of the artificial chordae tendineae implantation system is finely adjusted, such that the leaflet enters a clamping space defined between the distal clamp 310 and the proximal clamp 320. The second handle 301 is withdrawn toward the proximal end, and the clamping push rod 330 is driven to move toward the proximal end. Accordingly, the distal clamp 310 is moved close to the proximal clamp 320, that is, the clamping device 300 is in a clamping state, as illustrated in FIG. 11. At this time, the leaflet is firmly clamped by the clamping device 300. The proximal clamp 320, the distal clamp 310, and the pushing shaft 210 cooperatively form a smooth external surface, for facilitating moving the artificial chordae tendineae implantation system and reducing damage to heart tissue. It can be understood that, the distal clamp 310 may be moved away from the proximal clamp 320 via driving the first handle 201 toward the distal end. It also can be understood that, the distal clamp 310 may be moved away from the proximal clamp 320 via withdrawing the pushing shaft 210 and the first handle 201 toward the proximal end.

In the related art, the artificial chordae tendinea implanted by a U-shaped loop sleeve combined with a hook-shaped needle may cause an edge of leaflet to be folded and to be notched, and accordingly a matching edge may not be formed and mitral valve regurgitation may easily occur. As a result, the surgical effect is not ideal. In the artificial chordae tendineae implantation system of the present disclosure, since the chordae tendineae main body 110 is received in the clamping push rod 330, a distance between the artificial chordae tendineae and the edge of the leaflet is consistent, that is, the distance between the artificial chordae tendineae and the edge of the leaflet is the distance between the fixing cavity and the clamping push rod, which can effectively avoid the edge of the leaflet folding or a notch of the mitral valve, to enhance the surgical effect.

As illustrate in FIGS. 11 to 13 and 22 to 23, in order to improve the clamping effect, a clamping surface 321 disposed on the distal end of the proximal clamp 320 engages with a clamping surface 311 disposed on the proximal end of the distal clamp 310. The clamping surfaces 311, 321 each have a large contact area in contact with the leaflet. In an illustrative embodiment, the two clamping surfaces 311, 321 are slantingly disposed, that is, an angle formed between the clamping surface 311, 321 and an axis of the pushing shaft 210 is less than 90°. In addition, at least one of the clamping surfaces 311, 321 is provided with a reinforcing member for increasing clamping forces. In an illustrative embodiment, the reinforcing member is selected from a group consisting of a projection, a rib, a groove, and a recess provided on the clamping surface 311, 321. In this embodiment, the clamping surface 311 of the distal clamp 310 is provided with a number of ribs as the reinforcing member 312. The ribs are parallel to each other, and accordingly the clamping surface 311 is stepped.

As illustrated in FIGS. 22 to 23, the clamping push rod 330 is provided with an artificial chordae tendineae channel 331 for receiving the artificial chordae tendineae 100 along an axial direction. The distal clamp 310 is provided with an artificial chordae tendineae accommodation chamber 315 which is connected with the artificial chordae tendineae channel 331. The chordae tendineae main body 110 of the artificial chordae tendineae 100 is received in the artificial chordae tendineae channel 331 and the artificial chordae tendineae accommodation chamber 315.

The clamping surface 311 of the distal clamp 310 defines an accommodation slot 314 for accommodating the anti-slip member 130. The accommodation slot 314 is in communication with the artificial chordae tendineae accommodation chamber 315.

The clamping surface 311 of the distal clamp 310 further defines a fixing cavity 313 for receiving the fixing member 120 of the artificial chordae tendineae 100. The fixing cavity 313 is axially in communication with the artificial chordae tendineae accommodation chamber 315. The fixing cavity 313 is radially in communication with the accommodation slot 314. The fixing member 120 of the artificial chordae tendineae 100 is received in the distal clamp 310, corresponding to the puncture needle 410.

After the puncture needle 410 is connected to the fixing member 120, the puncture needle 410, the fixing member 120, the chordae tendineae main body 110, and the anti-slip member 130 are simultaneously driven out of the clamping surface 311 of the distal clamp 310 by driving the puncture needle 410 toward the proximal end, until the puncture needle 410, the fixing member 120, and the chordae tendineae main body 110 pass through the leaflet. The anti-slip member 130 is fitted on the upper surface of the leaflet.

The fixing cavity 313 is axially in communication with the artificial chordae tendineae accommodation chamber 315. The fixing member 120 of the artificial chordae tendineae 100 may be fixed in the fixing cavity 313 and smoothly pulled out of the fixing cavity 313 by an external force. Therefore, a shape of the fixing cavity 313 corresponds to a shape of the fixing member 120. A diameter of an inscribed circle of the fixing cavity 313 is larger than that of a circumscribed circle of the artificial chordae tendineae accommodation chamber 315. In an illustrative embodiment, a ratio of the diameter of the circumscribed circle of the artificial chordae tendineae accommodation chamber 315 to the diameter of the inscribed circle of the fixing cavity 313 is (0.2~0.4):1. When the fixing cavity 313 and the artificial chordae tendineae accommodation chamber 315 both have a cross section in a round shape, a diameter of an inscribed circle of the fixing cavity 313 is equal to that of a cross-section diameter of the fixing cavity 313, and a diameter of a circumscribed circle of the artificial chordae tendineae accommodation chamber 315 is equal to a cross-sectional diameter of the artificial chordae tendineae accommodation chamber 315. In this embodiment, the fixing cavity 313 has a cross section in a round shape, and a diameter of the fixing cavity 313 is D1. The artificial chordae tendineae accommodation chamber 315 has a cross section in a round shape, and a diameter of the artificial chordae tendineae accommodation chamber 315 is D2, where D2 is 30% of D1. If D2 is too large, when the puncture needle 410 is connected to the fixing member 120 of the artificial chordae tendineae 100 by pushing the puncturing push rod 420, the fixing member 120 may be moved from the fixing cavity 313 to the artificial chordae tendineae accommodation chamber 315 due to pushing forces of the puncturing push rod 420. As a result, the puncture needle 410 and the fixing member 120 of the artificial chordae tendineae 100 may not be successfully connected at one time, and the surgery time is prolonged. If D2 is too small, the chordae tendineae main body 110 of the artificial chordae tendineae 100 may not smoothly pass through the artificial chordae tendineae accommodation chamber 315. As a result, after the puncture needle 410 is connected to the fixing member 120 of the artificial chordae tendineae 100, the artificial chordae tendineae 100 may not be smoothly pulled out of the clamping surface 311 of the distal clamp 310.

In order to smoothly pull the chordae tendineae main body 110 and the anti-slip member 130 out of the clamping surface 311 of the distal clamp 310, the fixing cavity 313 is radially in communication with the accommodation slot 314. In an illustrative embodiment, a width of a communicating portion between the fixing cavity 313 and the accommodation slot 314 is D3, where D3 is 20%-50% of D1. If D3 is too large, the fixing member 120 of the artificial chordae tendineae 100 may not be firmly fixed in the fixing cavity 313 of the distal clamp 310. As a result, the fixing member 120 may easily slip out of the fixing cavity 313, and the artificial chordae tendineae implantation system fails. If D3 is too small, after the fixing member 120 is connected to the puncture needle 410, the fixing member 120 may not be smoothly pulled out of the fixing cavity 313, and accordingly, the surgery fails. It can be understood that, in other embodiments, the fixing cavity 313 and the artificial chordae tendineae accommodation chamber 315 both have a cross section in an elliptical, triangular, quadrangular, or polygonal shape as long as a shape of the fixing cavity 313 corresponds to a shape of the fixing member 120, and the shape of the artificial chordae tendineae accommodation chamber 315 does not affect that the chordae tendineae main body 110 smoothly slides in the fixing cavity 313.

In the related art, an artificial chordae tendineae is exposed outside of a device including the artificial chordae tendineae, such that an external surface of the device is not smooth. When entering a patient body, the device damages tissue of the patient due to friction and causes leakage of blood. As a result, risk of postoperative complications is increased. In the present disclosure, the fixing cavity 313 of the distal clamp 310 is configured to receive and fix the artificial chordae tendineae 100 in the artificial chordae tendineae implantation system. More importantly, the chordae tendineae main body 110 and the anti-slip member 130 may be pulled to the leaflet via the fixing cavity 313 without driving the distal clamp 310 to move away from the proximal clamp 320. In this way, when the distal clamp 310 is moved away from the proximal clamp 320, that is, a state of the clamping device 300 changes from the clamping state to the open state, the leaflet may be released from the clamping device 300 and resume flapping. At the moment of flapping resuming, the anti-slip member 130 is fitted on the upper surface of the leaflet. As such, a vigorous movement of leaflet relative to the chordae tendineae main body 110 and damage to the leaflet are avoided.

Compared with the related art, the artificial chordae tendineae implantation system provided by the embodiments of the present disclosure has advantages as follows.

The straight tapered tip of the puncture needle allows the puncturing point formed on the leaflet to be smaller, and accordingly damage to the leaflet is reduced.

The puncture needle and the artificial chordae tendineae are positioned via the clamping device, and accordingly the probability of successful connection between the puncture needle and the artificial chordae tendineae is increased, thereby shortening the surgery time.

In addition, a stable and reliable indirect connection between the puncture needle and the chordae tendineae main body of the artificial chordae tendineae may be formed via the fixing member. Thus, the artificial chordae tendineae may not easily detach from the puncture needle, and the artificial chordae tendineae may be quickly pulled to a fixed position.

As illustrated in FIG. 24, the artificial chordae tendineae implantation system according to a second embodiment of the present disclosure is an improvement based on the artificial chordae tendineae implantation system according to the first embodiment. The artificial chordae tendineae implantation system according to the second embodiment of the present disclosure is similar to the artificial chordae tendineae implantation system according to the first embodiment except that a puncturing device 400b is provided with two puncture needles 410 and two puncturing push rods 420 are respectively connected to the proximal end of the puncture needle 410. Proximal ends of the two puncturing push rods 420 are provided with a third handle 401. The two puncturing push rods 420 are received in the pushing shaft 210 parallelly. The first end and the second end of the chordae tendineae main body 110 of the artificial chordae tendineae 100 each are provided with the fixing member 120. The two fixing members 120 are respectively received in the distal clamp 310. The two puncture needles 410 respectively correspond to the two fixing members 120.

As illustrated in FIGS. 24, 25, and 26, the clamping push rod 330 is provided with the artificial chordae tendineae channel 331 along the axial direction. The distal clamp 310 defines two artificial chordae tendineae accommodation chambers 315 extending through the clamping surface 311 of the distal clamp 310. The two artificial chordae tendineae accommodation chambers 315 are connected through the artificial chordae tendineae channels 331. The two receiving chambers 315 are radially in communication with each other. The clamping surface 311 of the distal clamp 310 defines two fixing cavities 313 for respectively receiving the two fixing members 120. The two fixing cavities 313 are radially in communication with each other. Each of the fixing cavities 313 is axially in communication with the corresponding artificial chordae tendineae accommodation chamber 315. The ratio of the diameter D2 of the artificial chordae tendineae accommodation chamber 315 to the diameter D1 of the fixing cavity 313 is (0.2 to 0.4):1. The first end and the second end of the chordae tendineae main body 110 respectively extend through the two artificial chordae tendineae accommodation chambers 315 to be connected to the two fixing members 120 accommodated in the two fixing cavities 313.

After puncturing, the two puncture needles 410 are respectively connected to the two fixing members 120, such that the chordae tendineae main body 110, the two fixing members 120, and the two puncture needles 410 form a U-shaped structure. The chordae tendineae main body 110 is pulled out of the clamping surface 311 of the distal clamp 310 by driving the puncturing push rod 420 toward the proximal end. Part of the chordae tendineae main body 110 is fitted on the upper surface of the leaflet, and other parts of the chordae tendineae main body 110 together with the fixing member 120 and the puncture needle 410 pass through the leaflet until reaching the ventricular wall. Two chordae tendineae main bodies 110 can be simultaneously implanted between the leaflet and the ventricular wall. The anti-slip member 130 and part of the chordae tendineae main body 110 are fitted on the upper surface of the leaflet, which can limit the movement of the leaflet relative to the chordae tendineae main body 110 when the leaflet is flapping. Thus, damage to the leaflet is reduced.

In the embodiment, the chordae tendineae main body 110 may also be provided with the anti-slip member 130. As illustrated in FIG. 10, the first end and the second end of the chordae tendineae main body 110 of the artificial chordae tendineae 100 respectively pass through the two through holes 131 of the same anti-slip member 130. Thus, before puncturing, the chordae tendineae main body 110 and the anti-slip member 130 form a closed loop structure. After puncturing, the anti-slip member 130, the chordae tendineae main body 110, the two fixing members 120, and the two puncture needles 410 form a U-shaped structure. The chordae tendineae main body 110 presses the anti-slip member 130, such that the anti-slip member 130 abuts against the upper surface of the leaflet. The chordae tendineae main body 110, the anti-slip member 130, and the leaflet is substantially positioned.

As illustrated in FIGS. 25 and 26, the clamping surface 311 of the distal clamp 310 is further provided with the accommodation slot 314 for accommodating the anti-slip member 130. The two fixing cavities 313 are radially in communication with the accommodation slot 314. Therefore, after puncturing, the chordae tendineae main body 110 together with the two fixing members 120 and the anti-slip member 130 can be pulled out of the clamping surface 311 of the distal clamp 310. In an illustrative embodiment, the width D3 of the communicating portion between the fixing cavity 313 and the accommodation slot 314 is 20%-50% of the diameter D1 of the fixing cavity 313.

The working procedure of the artificial chordae tendineae implantation system according to the second embodiment of the present disclosure is described with the artifical chordae tendineae being implanted to the posterior leaflet of the mitral valve as an example.

Figure 32:
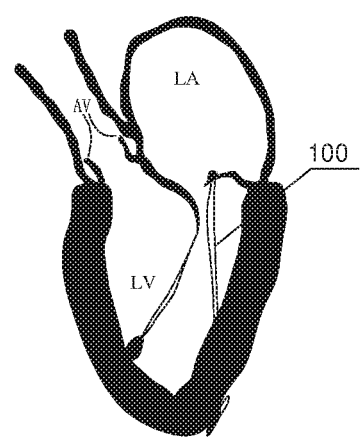

As illustrated in FIG. 27, the artificial chordae tendineae implantation system is driven into the left ventricle through a transapical approach. As illustrated in FIG. 28, the artificial chordae tendineae implantation system is further driven until that the distal clamp 310 and the proximal clamp 320 both are located in the left atrium. The second handle 301 is pushed toward the distal end to drive the clamping push rod 330 to move in the pushing shaft 210 toward the distal terminal. The distal clamp 310 is moved away from the proximal clamp 320 and is moved toward the distal end. At this time, the clamping space is formed between the proximal clamp 320 and the distal clamp 310 for clamping the leaflet. The relative positions of the first handle 201 and the second handle 301 keep unchanged, the artificial chordae tendineae implantation system is slowly moved towards the proximal end, till the leaflet enters into the clamping space formed between the proximal clamp 320 and the distal clamp 310. As illustrated in FIG. 29, the distal end of the artificial chordae tendineae implantation system is slightly moved until the edge of the leaflet is in contact with the clamping push rod 330. At this time, the second handle 301 is driven toward the proximal end to move the distal clamp 310 toward the proximal clamp 320 until the leaflet is clamped between the distal clamp 310 and the proximal clamp 320. The third handle 401 is pushed toward the distal end to drive the puncture needle 410 to move along the axis of the pushing shaft 210 toward the distal terminal, that is, the puncture needle 410 is moved toward the distal clamp 310, until that the puncture needle 410 passes through the leaflet and a fixed connection between the puncture needle 410 and the fixing member 120 of the artificial chordae tendineae 100 is formed. As illustrated in FIG. 30, the third handle 401 is withdrawn, such that the puncture needle 410 drives the fixing member 120 of the artificial chordae tendineae 100, the chordae tendineae main body 110 connected to the fixing member 120 sequentially to pass through the leaflet. At the same time, the anti-slip member 130 is pulled out of the clamping surface 311 of the distal clamp 310, the fitting surface (ie, a lower surface) of the anti-slip member 130 is in contact with the upper surface of a leaflet 900. Part of the chordae tendineae main body 110 presses the upper surface of the anti-slip member 130 such that the anti-slip member 130 is fitted on the leaflet 900, as illustrated in FIG. 31. The face contact between the anti-slip member 130 and the leaflet 900 can effectively reduce the risk of tearing the leaflet 900. As illustrated in FIG. 32, the third handle 401 is pulled back until the fixing member 120 is moved out of the proximal end of the pushing shaft 210. The artificial chordae tendineae implantation system is withdrawn. A length of the chordae tendineae main body 110 left in the heart is adjusted. The first end and the second end of the chordae tendineae main body 110 are respectively fixed to the ventricular wall or the papillary muscles.

Compared with the related art, the artificial chordae tendineae implantation system according to the second embodiment of the present disclosure has advantages as follows.

Multiple chordae tendineae bodies may be implanted at one time. Thus, the operation efficiency is improved. In addition, the contact between the artificial chordae tendineae and the leaflet is changed from point contact to face contact, and accordingly the artificial chordae tendineae can be effectively prevented from falling off from the anti-slip member and the leaflet. Thus, better surgery effect is ensured.

The anti-slip member is tightly fitted on the upper surface of the leaflet via the chordae tendineae main body. Reliable connections between the chordae tendineae main body, the anti-slip member, and the leaflet are formed. Thus, the leaflet is effectively prevented from being torn, the risk of the chordae tendineae main body and the anti-slip member falling off from the leaf surface is reduced, and better surgery effect is achieved.

The above description is only the exemplary embodiment of the present disclosure, and is not intended to limit the present disclosure. Any modifications, equivalent substitutions and improvements made within the spirit and principles of the present disclosure should be included in the protection scope of the present disclosure.

What is claimed is:

1. An artificial chordae tendinea implantation system, comprising:
   a fixing member;
   an artificial chordae tendineae comprising a flexible chordae tendineae main body, and at least one end of the chordae tendineae main body being connected with the fixing member;
   a pushing device comprising a pushing shaft, and the pushing shaft defining a plurality of lumens along an axis of the pushing shaft;
   a clamping device comprising a clamping push rod, a distal clamp, and a proximal clamp,
   wherein the distal clamp and the proximal clamp configured to cooperatively clamp a leaflet;
   the proximal clamp is disposed at a proximal end of the pushing shaft; the distal clamp is disposed at a distal end of the clamping push rod;
   a puncturing device comprising a puncture needle, and a distal end of the puncture needle being provided with a straight tapered tip;
   wherein the clamping device and the puncturing device are movably received in different lumens of the pushing shaft, the artificial chordae tendineae is received in the clamping device,
   and the fixing member is connected with the puncture needle;
   wherein the fixing member comprises a puncture connection member disposed at a side of the fixing member facing away from the chordae tendineae main body, and the puncture needle further comprises a chordae tendineae connection member configured to be connected with the puncture connection member;
   wherein the chordae tendineae connection member is disposed at a distal end of the puncture needle, the chordae tendineae connection member is at least one protruding tooth or a circle of protruding flanges configured to be connected with the puncture connection member in an interference fit connection, a snap connection, or a key connection; or the chordae tendineae connection member is threads, an adhesive layer, or a rough surface disposed on an external surface of the puncture needle.

2. The artificial chordae tendineae implantation system of claim 1, wherein the distal clamp comprises a clamping surface disposed at a proximal end of the distal clamp, the puncturing device further comprises a puncturing push rod connected to the puncture needle, wherein the puncturing push rod is received in the lumens of the pushing shaft, the clamping push rod defines an artificial chordae tendineae channel along an axis of the clamping push rod; the distal clamp defines an artificial chordae tendineae accommodation chamber; the artificial chordae tendineae accommodation chamber extends through the clamping surface; the artificial chordae tendineae channel is in communication with the artificial chordae tendineae accommodation chamber; the artificial chordae tendineae is received in the artificial chordae tendineae channel and the artificial chordae tendineae accommodation chamber.

3. The artificial chordae tendineae implantation system of claim 2, wherein the chordae tendineae main body is sleeved with an anti-slip member sliding along an axial of the chordae tendineae main body, and the clamping surface of the distal clamp defines an accommodation slot for accommodating the anti-slip member, and the accommodation slot is radially in communication with the artificial chordae tendineae accommodation chamber.

4. The artificial chordae tendineae implantation system of claim 3, wherein the fixing member is received in the distal clamp and the fixing member corresponds to the puncture needle.

5. The artificial chordae tendineae implantation system of claim 4, wherein the clamping surface of the distal clamp defines a fixing cavity therein for receiving the fixing member, the fixing cavity is axially in communication with the artificial chordae tendineae accommodation chamber, and the fixing cavity is radially in communication with the accommodation slot.

6. The artificial chordae tendineae implantation system of claim 5, wherein a shape of the fixing cavity corresponds to a shape of the fixing member, and a diameter of an inscribed circle of the fixing cavity is larger than a diameter of a circumscribed circle of the artificial chordae tendineae accommodation chamber.

7. The artificial chordae tendineae implantation system of claim 1, wherein the proximal clamp comprises a clamping surface disposed at a distal end of the proximal clamp, the clamping surface of the proximal clamp and the clamping surface of the distal clamp are capable of being fitted together, and at least one of the clamping surfaces comprises a reinforcing member.

8. The artificial chordae tendineae implantation system of claim 7, wherein the reinforcing member is selected from a group consisting of a protrusion, a ridge, a groove, and a recess provided on the clamping surface.

9. The artificial chordae tendineae implantation system of claim 1, wherein the distal clamp comprises a clamping surface disposed at a proximal end of the distal clamp, and the puncturing device comprises a pair of puncture needles and a pair of puncturing push rods connected to the pair of puncture needles respectively; the puncturing push rods are received in the lumens of the pushing shaft parallelly, and the chordae tendineae main body is provided with a pair of fixing members respectively disposed at two ends of the artificial chordae tendineae main body, and the pair of the fixing members is received in the distal clamp, and the pair of puncture needles respectively correspond to the pair of fixing members.

10. The artificial chordae tendineae implantation system of claim 9, wherein the clamping push rod defines an artificial chordae tendineae channel along an axis of the clamping push rod; the distal clamp defines two artificial chordae tendineae accommodation chambers, the two artificial chordae tendineae accommodation chambers extend through the clamping surface of the distal clamp; the two artificial chordae tendineae accommodation chambers are in communication with the artificial chordae tendineae channel; the two artificial chordae tendineae accommodation chambers are radially in communication with each other; the two ends of the achordae tendineae main body extend through the artificial chordae tendineae channel and the two artificial chordae tendineae accommodation chambers to be connected with the two fixing members, respectively.

11. The artificial chordae tendineae implantation system of claim 10, wherein the clamping surface of the distal clamp is provided with a pair of fixing cavities for respectively receiving the pair of fixing members, and each of the fixing cavities is axially in communication with the pair of artificial chordae tendineae accommodation chambers; and the pair of the fixing cavities are radially in communication with each other.

12. The artificial chordae tendineae implantation system of claim 11, wherein the chordae tendineae main body of the artificial chordae tendineae is sleeved with an anti-slip member, wherein the anti-slip member defines a pair of through holes, two ends of the chordae tendineae main body extend through the pair of through holes, respectively.

13. The artificial chordae tendineae implantation system of claim 12, wherein the clamping surface of the distal clamp defines a pair of fixing cavities for receiving the pair of fixing members and an accommodation slot for accommodating the anti-slip member, each of the fixing cavities is radially in communication with the accommodation slot, and the accommodation slot is radially in communication with the artificial chordae tendineae accommodation chamber.

\* \* \* \* \*